United States Patent [19]

Wilson, Jr. et al.

[11] Patent Number: 5,744,685

[45] Date of Patent: Apr. 28, 1998

[54] UNSATURATED HYDROCARBON SEPARATION AND RECOVERY PROCESS

[75] Inventors: Robert B. Wilson, Jr., Palo Alto, Calif.; Karen Meyer, Cincinnati, Ohio; Marianna F. Asaro, Belmont, Calif.

[73] Assignee: Amoco Corporation, Chicago, Ill.

[21] Appl. No.: 732,514

[22] Filed: Oct. 15, 1996

[51] Int. Cl.$^6$ .............................. C07C 7/00; C07C 7/10; C07C 7/152

[52] U.S. Cl. .................. 585/811; 585/809; 585/833; 585/842; 585/850; 585/855; 585/856

[58] Field of Search .......................... 585/809, 811, 585/833, 842, 850, 855, 856

[56] References Cited

U.S. PATENT DOCUMENTS

| | | | |
|---|---|---|---|
| 5,391,791 | 2/1995 | DuBois et al. | 556/60 |
| 5,414,194 | 5/1995 | Dubois et al. | 585/855 |
| 5,430,225 | 7/1995 | DuBois et al. | 585/855 |

OTHER PUBLICATIONS

Murata et al., J. Am. Chem. Soc., vol. 116, pp. 3389–3398, 1994.

DuBois et al., J. Am. Chem. Soc., vol. 101, pp. 5245–5252 (1979).

DuBois et al., J. Am. Chem. Soc., vol. 102, pp. 7456–7461 (1980).

DuBois et al., Inorg. Chem., vol. 20, pp. 3064–3071 (1981).

McKenna et al., J. Am. Chem. Soc., vol. 105, pp. 5329–5337 (1983).

Birnbaum et al., Organometallics, vol. 10, pp. 1779–1786 (1991).

*Primary Examiner*—Glenn Caldarola
*Assistant Examiner*—Thuan D. Dang
*Attorney, Agent, or Firm*—Robert A. Yesukevich; Frank J. Sroka; James R. Henes

[57] ABSTRACT

A process is disclosed for the separation and recovery of an unsaturated hydrocarbon from its mixture with at least one other material by the selective and reversible complexation of the unsaturated hydrocarbon using a single cubane-type cluster of palladium, molybdenum and sulfur as a complexation agent.

17 Claims, No Drawings

UNSATURATED HYDROCARBON SEPARATION AND RECOVERY PROCESS

BACKGROUND OF THE INVENTION

1. Field of the Invention

The present invention relates to a process for the separation and recovery of an unsaturated hydrocarbon from a mixture thereof with at least one other component by the selective and reversible complexation of the unsaturated hydrocarbon, and more particularly concerns the aforesaid process using a single cubane-type cluster of palladium, molybdenum and sulfur as the complexation agent.

2. Discussion of the Prior Art

Processes for separating unsaturated hydrocarbons from a gaseous hydrocarbon mixture by contacting the mixture with an aqueous solution of heavy metal salts capable of forming reversible complexes with the unsaturated hydrocarbons, whereby the unsaturated hydrocarbons are complexed and extracted by such aqueous solution, are well-known. Water-soluble silver or copper salts or complexes have been reported as being capable of forming reversible complexes with unsaturated hydrocarbons in such processes. However, at least some of such salts or complexes are reported to be adversely affected by certain materials that are frequently present in the gaseous mixtures from which the unsaturated hydrocarbons are to be separated or to form complexes with alkenes or alkynes that are thermally unstable.

Thus, it is highly desirable to develop improved complexing agents for use in the aforesaid processes for separating unsaturated hydrocarbons from hydrocarbon mixtures containing them. Dubois et al., U.S. Pat. Nos. 5,391,791; 5,414,194; and 5,430,225 disclose novel molybdenum sulfide dimer compounds and their use in olefin separation and acetylene removal processes. The disclosed dimers act as complexation agents for the olefins and acetylenes wherein the sulfide ligands of the molybdenum-sulfide dimers act as the site of olefin binding. The dimers disclosed have the general formula

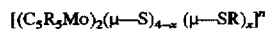

$[(C_5R_5Mo)_2(\mu—S)_{4-x}(\mu—SR)_x]^n$ where x is 0–3 and n is 0, +1, or −1. In addition, this structure can be modified in a limited number of ways, such as substitutions that can be made to the alkanedithiolate moiety R or to the cyclopentadienyl moiety $C_5H_5$, in order to enhance the water solubility of the dimer or to introduce chemically reactive ligands that can be used to incorporate the dimer within the matrix of polymeric materials, such as membranes. The patents define suitable water soluble molybdenum-sulfide dimers as including all compounds that contain molybdenum and sulfur and that are capable of forming chemically or thermally-reversible alkanedithiolate or alkenedithiolate complexes that have significant solubility in water or aqueous systems.

The dimeric complexation agents are disclosed as being useful in separation processes that include liquid/liquid, gas/liquid, liquid/solid and gas/solid separation procedures that are familiar to those skilled in the art. Separations by the use of the molybdenum-sulfide dimers that are disclosed include the separation of olefins from paraffins (for example, ethylene from ethane and propylene from propane), the separation of olefins (for example, ethylene from propylene), the separation of olefin isomers (for example, cis-2-butene from trans-2-butene), the separation of olefins from alkynes (for example, ethylene from acetylene and propylene from propyne), and the removal of alkynes from a gaseous hydrocarbon feed stream and the catalytic reduction of alkynes.

The molybdenum sulfide dimers disclosed in the aforesaid Dubois et al. patents were synthesized in accordance with the procedures of Dubois et al., J. Am. Chem. Soc., Volume 101, pages 5245–5252 (1979); Dubois et al., J. Am. Chem. Soc., Volume 102, page 7456 (1980); Dubois et al., Inorg. Chem., Volume 20, pages 3064–3071 (1981); M. McKenna et al., J. Am. Chem. Soc., Volume 105, pages 5329–5337 (1983); and J. Birnbaum et al., Organometallics, volume 10, pages 1779–1786 (1991). However, generally such syntheses are lengthy and complicated and afford a low yield of the desired product. Also the product formed often must be modified further in order to achieve the necessary water solubility. Consequently, it is highly desirable to develop alternative materials that could be used as suitable complexation agents for the selective and reversible complexation of unsaturated hydrocarbons in the aforesaid processes for separating unsaturated hydrocarbons from multi-component gaseous mixtures containing them.

Murata et al., J. Am. Chem. Soc., Volume 116, pages 3389–3398 (1994) discloses the reaction between palladium black and an incomplete cubane-type cluster having the formula $[Mo_3S_4(H_2O)_9]Cl_4$ to form a novel mixed-metal cubane-type cluster having the formula $[Pd\ Mo_3\ S_4(H_2O)_9Cl]Cl_3$. Treatment of this product (a) with 1,4,7-triazacyclononane (tacn) afforded a well defined single cubane-type cluster $[Pd\ Mo_3\ S_4(tacn)_3Cl]Cl_3$ or (b) with 4-toluenesulfonate (TsO) afforded a double cubane-type cluster having the formula $[Pd_2Mo_6S_8(H_2O)_{18}](OTs)_8$, in which two $PdMo_3\ S_4$ units are connected by two Pd—S bonds. The single cubane-type cluster $[PdMo_3\ S_4(tacn)_3Cl]Cl_3$ could be modified to form a single cubane-type cluster $[Pd\ Mo_3\ S_4(tacn)_3(L)]^{+4}$ wherein L is an alkene coordinated to the palladium site, by contrast to the molybdenum sulfide dimers discussed above wherein the sulfide ligands, not the metal, act as the site of olefin bonding. The use of an aforesaid single cubane-type cluster—that is, $[Pd\ Mo_3\ S_4(H_2O)_9Cl]Cl_3$ or $[PdMo_3S_4(tacn)_3Cl]Cl_3$—as a complexation agent to selectively and reversibly complex an unsaturated hydrocarbon in a process for the separation and recovery of an unsaturated hydrocarbon from mixtures of it with other materials was not investigated or proposed.

OBJECTS OF THE INVENTION

It is therefore a general object of the present invention to provide an improved aforesaid process of separation and recovery that affords the aforesaid desirable features and overcomes the aforesaid problems.

More particularly, it is an object of the present invention to provide an improved aforesaid process that employs a complexation agent that is soluble and stable in water and that selectively forms a reversible complex with an unsaturated hydrocarbon that is also soluble and stable in water.

It is another object of the present invention to provide an improved aforesaid process that employs a complexation agent that can be prepared by a relatively uncomplicated synthesis.

It is a further object of the present invention to provide an improved aforesaid process that employs a complexation agent whose stability and complexation activity are not adversely affected by other materials that are frequently present in the multi-component gaseous mixtures from which an unsaturated hydrocarbon is to be separated.

Other objects and advantages of the present invention will become apparent upon reading the following description and appended claims.

SUMMARY OF THE INVENTION

These objects are achieved by the process of the present invention for the separation and recovery of at least one unsaturated hydrocarbon from a mixture thereof with at least one other component in a multi-component feed gas, comprising: (a) contacting the feed gas and an acidic, aqueous liquid solution of a single cubane-type cluster of the formula [(H$_2$O)$_9$Mo$_3$S$_4$Pd X]X$_3$ wherein X is a halide ion, with the solution being at least 2 molar in a hydrohalic acid, as a complexation agent, under conditions such that the aforesaid complexation agent has a substantially greater affinity to form, and does selectively form, at least one water-soluble complex with the at least one unsaturated hydrocarbon than with the aforesaid at least one other component, such that a substantial portion of the aforesaid at least one unsaturated hydrocarbon thereby dissolves in the aqueous solution; (b) separating the resulting aqueous solution from the feed gas; (c) contacting the aqueous solution from step (b) with a gas phase under conditions such that the aforesaid at least one complex dissociates and the resulting at least one dissociated unsaturated hydrocarbon is stripped from the aqueous solution into the gas phase; and (d) separating the resulting gas phase from the aqueous solution.

DETAILED DESCRIPTION OF THE PREFERRED EMBODIMENTS

The method of the present invention is useful for separating at least one unsaturated hydrocarbon, such as an alkene, alkyne or aromatic compound, from a mixture thereof with at least one other component, such as an alkane, another unsaturated hydrocarbon, or an inorganic gas like hydrogen or nitrogen, in a wide variety of multi-component gas streams. Suitable streams include many streams that are typically present in petroleum refineries and chemical plants. The streams in a petroleum refinery or chemical plant that are especially suitable as the multi-component feed gas in the method of the present invention are waste streams or recycle streams. Such streams often contain mixtures of either ethylene and ethane or propylene and propane, or both such mixtures, as well as other components. For example, offgas from a catalytic cracking unit in a refinery generally contains a mixture of ethylene, ethane, methane and hydrogen. In addition, the feed to an alkylation unit typically contains propylene admixed with contaminant propane; and separation of the propylene from propane would permit the use of a feed stream having a higher propylene content and thereby an effective debottlenecking of the alkylation unit. In chemical plants, ethylene is invariably present in a recycle stream employed as a portion of the feed to an olefins production unit and in an overhead stream from a demethanizer employed in the treatment of the resulting olefins products. Ethylene or propylene or both are also components in various vent streams or as contaminants in various feedstocks in chemical plants. All such streams are suitable sources of mixtures from which one or more unsaturated hydrocarbon can be separated by the method of the present invention. In general, the numerous processes that produce streams containing dilute unsaturated hydrocarbon products are sources of feed stream for the method of the present invention.

The reactivity of unsaturated hydrocarbons, for example, unsaturated aliphatic hydrocarbons, with the complexation agent employed in the method of the present invention generally decreases from acetylenes to dienes to monoolefins; and many other materials such as saturated hydrocarbons, in particular, saturated aliphatic hydrocarbons, and inorganic gases like nitrogen or hydrogen, are essentially unreactive towards the complexation agent employed in the method of the present invention. In addition, the various members of a given one of these aforesaid types of unsaturated aliphatic hydrocarbons often exhibit different reactivities towards the complexation agent employed in the method of the present invention. Thus, on the basis of such differences, the process of the present invention can be used to separate paraffins from monoolefins, diolefins from monoolefins, diolefins from acetylenes, or acetylenes from paraffins, monoolefins and diolefins; as well as to separate a given unsaturated aliphatic hydrocarbon in one of the aforesaid classes from another member of the same class where different members of the same class react with the complexation agent employed in the method of the present invention to form complexes of different stability or at different rates.

In the method of the present invention, the mixture of the unsaturated hydrocarbon or hydrocarbons with at least one other component in the feed gas is contacted with an acidic, aqueous liquid solution of the single cubane-type cluster of the formula

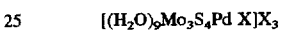
[(H$_2$O)$_9$Mo$_3$S$_4$Pd X]X$_3$ where X is a halide ion, preferably chloride or bromide, with the solution being 2 molar in a hydrohalic acid, preferably hydrochloric acid, as the complexation agent.

This complexation agent is prepared in accordance with the following two-step procedure when, for example, X is chloride:

3(NH$_4$)$_2$MoS$_4$+NaBH$_4$+4HCl→[(H$_2$O)$_9$Mo$_3$S$_4$]Cl$_4$+8H$_2$S+salts (1)

[(H$_2$O)$_9$Mo$_3$S$_4$]Cl$_4$+Pd→[(H$_2$O)$_9$Mo$_3$S$_4$PdCl]Cl$_3$ (2)

The starting material (NH$_4$)$_2$MoS$_4$ is commercially available or can be prepared by the reaction of Na$_2$MoO$_4$ with H$_2$S in NH$_4$OH, as reported by J. W. McDonald et al., "Syntheses and Characterization of Ammonium and Tetraalkylammonium Thiomolybdates and Thiotungstates," Inorganica Chimica Acta, volume 72, pages 205–210, (1983). One illustrative preparation reported in T. Shibahara et al., "Syntheses and Electrochemistry of Incomplete Cubane-Type Clusters with M$_3$S$_4$ Cores (m=Mo,W). X-Ray Structures of [W$_3$S$_4$(H$_2$O)$_9$](CH$_3$C$_6$H$_4$SO$_3$)$_4$·9H$_2$O·Na$_2$ [W$_3$S$_4$(Hnta)$_3$]5H$_2$O and (bpy H)$_5$[W$_3$S$_4$(NCS)$_9$]·3H$_2$O, " Inorg. Chem., Volume 31, pages 640–647 (1992), performs step 1 in two stages. Based on such preparation, the first such stage was conducted in a 50-liter reactor to which is added 20 liters of an aqueous solution of 879 grams of (NH$_4$)$_2$MoS$_4$ that is then cooled to about 0°–10° C. Additions to the aqueous solution in the reactor of 8 liters of an aqueous solution of 870 grams of NaBH$_4$ and 8 liters of 12M HCl were made in alternating 40–50 milliliter aliquots over 2 hours with vigorous stirring. During the additions, the temperature of the reaction mixture rose to 41° C. At the end of the additions, a final quantity of 10 liters of 12M HCl was added. In the second such stage, the reaction mixture was then transferred to a 100 liter reactor equipped with a heating mantle and air sparge inlet. The reaction mixture was heated to reflux, with rapid stirring and with air bubbled through the reaction mixture to oxidize the complex. The reaction was allowed to proceed for about 20 hours, after which time the reaction mixture was filtered twice. The first filtration was through coarse filter paper to remove salts, and the second filtration was through a fine filter. After the filtrations were done, the solution was loaded onto a Shephadex column and chromotographed using 2N hydrochloric acid as eluent to collect the green product. The column was prepared from 2 kilograms of Shephadex in water.

The resulting trimer was produced at a 50–70 mole percent yield and had the following structure:

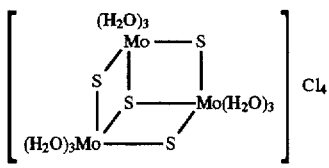

The formation of the palladium derivative in step (2) was achieved generally by the synthesis disclosed in Murata et al. "Synthesis of Mixed-Metal Sulfide Cubane-Type Clusters with the Novel PdMo$_3$S$_4$ Core and Reactivities of the Unique Tetrahedral Pd Site Surrounded by Sulfide Ligands toward Alkenes, CO, BuNc, and Alkynes," J. Am. Chem. Soc., volume 116, pages 3389–3398 (1994). Although the reaction in step (2) of the trimer with palladium black is reported in Murata et al. to require a 10 mole excess of palladium metal, a 2 mole excess of palladium metal was found to be sufficient.

In step 2, the reaction mixture from step (1), which weighed 1124 grams in 3.5 liters of 2 normal hydrochloric acid was degassed with argon and 166 grams of palladium black was added to it. The reaction mixture was kept under an argon atmosphere and was stirred for the entire 24 hour reaction period. The reaction solution was then filtered under argon. The solution of the palladium-containing cubane-type cluster was transferred under an argon atmosphere into evacuated amber bottles which were then sealed with sure seal caps. The resulting palladium derivative was produced at an approximately 80 weight percent yield and had the following structure:

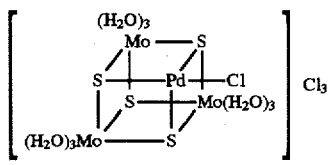

Experimental tests indicate that the resulting palladium-containing single cubane-type cluster has all of the necessary characteristics to serve as an effective complexation agent in the method of the present invention. It is soluble in water at a level of 0.48 moles per liter. In addition, this palladium-containing complexation agent functions very efficiently to complex unsaturated hydrocarbons in the method of the present invention. For example, when contacted with propylene, from 9 to 15 mole percent of the propylene is taken up in only a 2-milliliter volume of a 0.48 molar solution of the palladium-containing complexation agent in either water or 2 molar hydrochloric acid. Furthermore, the complexation reaction is completely reversible, and a purge with argon or nitrogen at room temperature is sufficient to remove the unsaturated hydrocarbon from the solution of the aforesaid complexation agent.

Furthermore, this palladium-containing single cubane-type cluster demonstrated unique activity as a complexation agent in the method of the present invention. For example, when other metals, such as silver, gold, nickel, iron, mercury, or copper, are employed instead of palladium in step (2) of the above synthesis, the results are substantially different than when palladium is employed. In particular, when silver or gold is employed instead of palladium in step (2), neither silver nor gold reacts with the molybdenum-sulfide trimer, and a silver- or gold-containing cubane-type cluster is not formed. When iron, mercury or elemental copper is employed instead of palladium in step (2), iron-, mercury- or copper-containing cubane-type clusters are formed but do not react or complex with an unsaturated hydrocarbon. Similarly, the palladium-free product of equation (1) hereinabove does not react or complex with an unsaturated hydrocarbon. In addition, the double cubane-type cluster formed by reaction of [(H$_2$O)$_9$Mo$_3$S$_4$, Pd Cl]Cl$_3$ with 4-toluenesulfonate (TsO), as reported in Murata et al., does not react or complex with unsaturated hydrocarbons. When nickel or cuprous ion is employed instead of palladium in step (2), a nickel- or copper-containing cubane-type cluster is formed but each reacts with unsaturated hydrocarbons to form irreversible complexes. Thus [(H$_2$O)$_9$Mo$_3$S$_4$PdX]X$_3$ is uniquely suitable as a complexation agent in the method of the present invention.

Furthermore, replacement of the halide ion as the counter anion in the palladium-containing complexation agent employed in the method in the present invention results in either the failure of the complexation agent to complex unsaturated hydrocarbons or the formation of irreversible or unstable complexes between the complexation agent and unsaturated hydrocarbons. This is the case even when the replacement counter-anion is borofluoride (BF$_4$).

In addition, the aforesaid palladium-containing complexation agent is employed in the method of the present invention in an acidic aqueous solution in which hydrochloric or hydrobromic acid is the acid and is present at a concentration of at least 2 molar. When hydrochloric or hydrobromic acid is replaced in the aqueous solution by another acid, for example, sulfuric acid, there is a drastic reduction in the relative amount of unsaturated hydrocarbon that is complexed by the aforesaid complexation agent and extracted into the aqueous solution. Furthermore, the complexation agent employed in the method of the present invention is more stable and soluble in at least 2 molar hydrochloric or hydrobromic acid solution in water than in water alone.

Many of the streams in a petroleum refinery or chemical plant that are especially suitable as the multi-component feed gas in the method of the present invention contain components which may have an adverse effect on the stability or complexation activity of the aforesaid complexation agent. Consequently, an important characteristic of the complexation agent employed in the method of this invention is its stability and complexation activity in the presence of such potentially harmful components in the feed gas. Experimental tests indicate that the stability and complexation activity of the complexation agent employed in the method of this invention are not adversely affected by hydrogen, COS, acetylene, methyl acetylene, propylenediene or calcium chloride in the feed gas. In addition, the complexation agent employed in the method of this invention is stable in the presence of oxygen or air for up to 4 days, after which time the complexation agent undergoes decomposition. Furthermore, even when the feed gas contains 50 weight percent of hydrogen at a pressure of from 15 to 150 pounds per square inch gauge, the complexation agent complexes the unsaturated hydrocarbon but does not significantly promote hydrogenation of olefins to paraffins. However, the complexation agent employed in the method of this invention does suffer a slight loss in its activity when carbon monoxide is present in the feed gas and is unstable when hydrogen sulfide is present in the feed gas.

The process of the present invention is performed by contacting in step (a) the aforesaid feed gas and an acidic aqueous liquid solution of the aforesaid complexation agent under conditions such that the complexation agent has a substantially greater affinity to form, and does selectively form, at least one water-soluble complex with the at least one unsaturated hydrocarbon component than with the aforesaid at least one other component of the feed gas, such that a substantial portion of the at least one unsaturated hydrocarbon component thereby dissolves in the aqueous solution. Thereafter the resulting aqueous solution is separated in step (b) from the feed gas, and contacted in step (c) with a gas phase, preferably a stripping gas, under conditions such that the aforesaid at least one complex dissociates and the resulting at least one dissociated unsaturated hydrocarbon is stripped from the aqueous solution into the gas phase. The resulting gas phase is then separated from the aqueous solution in step (d).

The conditions employed in step (a) comprise a first temperature, first pressure, concentration of the complexation agent in the aqueous solution, pH of the aqueous solution, relative amounts of the aqueous solution and feed gas, and length of contact time, at which the complexation agent is soluble and stable in the aqueous solution and at which the complexation agent complexes a substantial portion of the at least one unsaturated hydrocarbon to form a complex that is stable and soluble in the aqueous solution. When the unsaturated hydrocarbon is ethylene or propylene, the first temperature is in the range of from about 0° C., preferably from about 20° C., more preferably from about 25° C., to about 200° C., preferably to about 200° C., more preferably to about 70° C.; and the first pressure is in the range of from about 0, preferably from about 15, more preferably from about 15, to about 600, preferably to about 600, more preferably to about 300 pounds per square inch gauge.

The conditions employed in step (c) comprise a second temperature, second pressure, relative amounts of the aqueous solution and gas phase, the length of contact time, and optionally the use of a stripping or purge gas, at which the complex(es) containing the unsaturated hydrocarbon(s) dissociates and the dissociated unsaturated hydrocarbon is stripped from the aqueous solution into the gas phase. When the unsaturated hydrocarbon is ethylene or propylene, the second temperature is in the range of from about 0° C., to about 200° C. and the second pressure in the range of from about 0 to about 600 pounds per square inch gauge, and either the second temperature is from about 0° C., preferably from about 0° C., more preferably from about 0° C. to about 99° C., preferably to about 50° C., more preferably to about 35° C. higher than the first temperature employed in step (a), or the second pressure is from about 0, preferably from about 0, more preferably from about 0, to about 500, preferably to about 300, more preferably to about 50 pounds per square inch gauge lower than the first pressure employed in step (a), or both.

Preferably, the gas phase employed in step (c) is a stripping or purge gas that flows through or in contact with the aqueous liquid solution. However, such gas phase can also be a stationary gas under vacuum or substantially reduced pressure and in contact with the aqueous liquid solution.

Any convenient conventional method can be employed for the performance of each of steps (a) and (c) in the method of the present invention. In addition, steps (a) and (c) can be performed by the same method or by different methods. For example, facilitated transport membrane technology is a known separation technique that would be suitable for the practice of steps (a) and(c) in the method of the present invention. It has been demonstrated in the laboratory for the selective separation of gas stream components, such as the removal of olefins from hydrocarbon-containing feed streams. Sirkar, U.S. Pat. No. 4,750,918 discloses a type of facilitated transport involving the use of hollow fiber membranes, as opposed to flat sheet membranes. In this disclosure, the feed and recovery hollow fibers are immersed in a liquid bath to avoid drying problems often encountered with flat sheet immobilized membranes. The gases permeate through the wall of the feed hollow fiber, diffuse across the liquid bath and permeate into the bore of the recovery hollow fiber.

S. Majumdar, et al., "A New Liquid Membrane Technique for Gas Separation," A. I. Ch. E. Journal, Volume 34., No. 7, pages 1135–1145, discloses a liquid membrane separation technique for gas mixtures in which feed and sweep gases flow through the lumen of two different sets of hydrophobic microporous hollow fibers while a liquid on the shell side acts as the membrane. The technique involves the use of a dense population of hydrophobic microporous hollow fibers of small outside diameter and a permeator shell. In such a hollow-fiber assembly, the space between the adjacent fibers is filled with an aqueous liquid chosen to function as a liquid membrane. One set of hollow fibers carries the high-pressure feed gas while a second set of hollow fibers carries a sweep gas, usually at a pressure considerably lower than the feed pressure. Ideally, the fiber bundle is arranged in such a way that a feed-gas-carrying fiber is immediately adjacent to a sweep-gas-carrying fiber. Water and aqueous electrolytic solutions do not penetrate the pores in these hydrophobic fibers unless the liquid pressure exceeds 10–15 atmospheres. The feed gas species contact the membrane liquid at the pore mouths of the feed fiber outside surface. They dissolve at this feed gas-membrane liquid interface and diffuse through the liquid membrane to the open pores of the nearest sweep fiber, where they desorb. The desorbed gases are carried away through the sweep fiber lumina by an inert sweep gas. The membrane liquid between the fibers is usually stationary.

Z. Qi et al., "Microporous Hollow Fibers for Gas Absorption," J. Membrane Sci., Volume 23, page 321 (1985) discloses the use of two hydrophobic microporous hollow-fiber modules for gas separation, one in the sorption mode and the other in the desorption mode. R. Creusen et al., European Patent Application No. 94201995.1, filed on Jul. 11, 1994 and published on Jan. 18, 1995 as Publication No. 0634204 A1, discloses a process and device for the separation of an unsaturated hydrocarbon from a fluid mixture with other hydrocarbons in which in a first stage the fluid mixture is passed at superatmospheric pressure to one side of a first semiselective gas separation membrane with a non-porous active layer, and a liquid complexing agent is passed along the other side of such first membrane, where the unsaturated hydrocarbon is bound through complexation at the interface of the membrane and the complexing agent. In a second stage, the unsaturated hydrocarbon is dissociated from the complexing agent through a temperature increase, and the resulting mixture of the complexing agent and dissociated unsaturated hydrocarbon is separated, and the complexing agent is then recycled. Preferably the mixture of complexing agent and dissociated, unsaturated hydrocarbon is passed at superatmospheric pressure to one side of a second semiselective membrane with a non-porous active layer wherein the unsaturated hydrocarbon migrates to the other side of the second membrane and is discharged. The disclosed advantage of such process and device is that the process of sorption involving the complexation reaction in the first stage is separate and independently adjustable from the process of desorption involving the dissociation reaction in the second stage and that a substantial dissociation of the complex formed can be obtained by using a temperature increase.

From the above description it is apparent that the objects of the present invention have been achieved. While only certain embodiments and various modifications have been described, numerous alternative embodiments and various modifications will be apparent from the above description to those skilled in the art. These alternatives and embodiments are considered equivalents and within the spirit and scope of the present invention.

Having described the invention, what is claimed is:

1. A process for the separation and recovery of at least one unsaturated hydrocarbon from a mixture thereof with at least one other component in a multi-component feed gas, comprising:

(a) contacting the feed gas and an acidic aqueous liquid solution of a single cubane-type cluster of the formula

$[(H_2O)_9Mo_3S_4Pd\,X]X_3$ wherein X is a halide ion, and at least 2 molar in a hydrohalic acid as a complexation agent, under conditions such that the aforesaid complexation agent has a substantially greater affinity to form, and does selectively form, at least one water-soluble complex with the at least one unsaturated hydrocarbon than with the aforesaid at least one other component, such that a substantial portion of the aforesaid at least one unsaturated hydrocarbon thereby dissolves in the aqueous solution;

(b) separating the resulting aqueous solution from the feed gas;

(c) contacting the aqueous solution from step (b) with a gas phase under conditions such that the aforesaid at least one complex dissociates in the aqueous solution and the resulting at least one dissociated unsaturated hydrocarbon is stripped from the aqueous solution into the gas phase; and (d) separating the resulting gas phase from the aqueous solution.

2. The process of claim 1 wherein X is chloride or bromide and the aqueous liquid solution employed in step (a) is at least 2 molar in hydrochloric or hydrobromic acid.

3. The process of claim 1 wherein the conditions employed in step (a) comprise a first temperature and a first pressure and wherein the first temperature is in the range of from about 0° C. to about 200° C. and the first pressure is in the range of from about 0 to about 600 pounds per square inch gauge.

4. The process of claim 3 wherein the first temperature is in the range of from about 20° C. to about 200° C.

5. The process of claim 4 wherein the first temperature is in the range of from about 25° C. to about 70° C.

6. The process of claim 3 wherein the first pressure is in the range of from about 15 to about 600 pounds per square inch gauge.

7. The process of claim 6 wherein the first pressure is in the range of from about 15 to about 300 pounds per square inch gauge.

8. The process of claim 1 wherein the gas phase in step (c) is a stripping or purge gas.

9. The process of claim 1 wherein the conditions employed in step (c) comprise a second temperature and a second pressure, wherein the second temperature is in the range of from about 0° C. to about 200° C. and the second pressure in the range of from about 0 to about 600 pounds per square inch gauge, and either the second temperature is from about 0C to about 99° C. higher than the first temperature employed in step (a) or the second pressure is from about 0 to about 500 pounds per square inch gauge below the first pressure employed in step (a), or both.

10. The process of claim 9 wherein the second temperature is from about 0° C. to about 50° C. higher than the first temperature employed in step (a).

11. The process of claim 10 wherein the second temperature is from about 0° C. to about 35° C. higher than the first temperature employed in step (a).

12. The process of claim 9 wherein the second pressure is from about 0 to about 300 pounds per square inch gauge lower than the first pressure employed in step (a).

13. The process of claim 12 wherein the second pressure is from about 0 to about 50 pounds per square inch gauge lower than the first pressure employed in step (a).

14. The process of claim 1 wherein the unsaturated hydrocarbon comprises at least one of ethylene and propylene and the aforesaid other component from which the unsaturated hydrocarbon is separated comprises at least one of ethane, propane, nitrogen and hydrogen.

15. The process of claim 1 wherein the feed gas comprises at least two unsaturated hydrocarbons.

16. The process of claim 15 wherein in step (a) each unsaturated hydrocarbon in the feed gas forms a complex with the aforesaid complexation agent, and in step (c) each aforesaid complex dissociates and the resulting dissociated unsaturated hydrocarbons are stripped together from the aqueous solution into the gas phase in a single stage.

17. The process of claim 9 wherein the feed gas comprises at least two unsaturated hydrocarbons, each of which forms in step (a) a complex with the aforesaid complexation agent, and in step (c) at least one aforesaid complex dissociates and the resulting at least one dissociated unsaturated hydrocarbon is stripped from the aqueous solution into the gas phase and at least one unsaturated hydrocarbon remains complexed with the complexation agent in the aqueous solution and is separated therein from the gas phase in step (d) and wherein the separated aqueous solution is thereafter contacted in step (e) with a gas phase under conditions such that at least one aforesaid complex therein dissociates and the resulting at least one dissociated unsaturated hydrocarbon is stripped into the gas phase which is then separated from the aqueous solution in step (f).

* * * * *